United States Patent [19]

Matuura et al.

[11] Patent Number: 5,179,006
[45] Date of Patent: Jan. 12, 1993

[54] PROCESS FOR MEASURING ENDOTOXIN

[75] Inventors: Shuji Matuura, Kawanishi; Masakazu Tsuchiya, Itami, both of Japan

[73] Assignee: Wako Pure Chemical Industries, Ltd., Osaka, Japan

[21] Appl. No.: 313,829

[22] Filed: Feb. 23, 1989

[30] Foreign Application Priority Data

Feb. 27, 1988 [JP] Japan .................................. 63-45069

[51] Int. Cl.$^5$ .......................... C12Q 1/37; C12Q 1/34; C12Q 1/04
[52] U.S. Cl. ........................................ 435/23; 435/18; 435/34
[58] Field of Search ............................. 435/23, 18, 34

[56] References Cited

FOREIGN PATENT DOCUMENTS 58-13516 1/1983 Japan .
59-27828 2/1984 Japan .

OTHER PUBLICATIONS

"Gelatin of Limulus Amoebocyte Lysate by an Antitumor $(1\rightarrow 3)$-$\beta$-D-Glucan", Kakinuma et al, *Biochemical and Biophysical Research Communications*, vol. 101, No. 2, 1981, Jul. 30, 1981, pp. 434–439.

"Bacterial Endotoxin, Chemical, Biological and Clinical Aspects", Homma et al, *Verlag Chemie*, pp. 365–382.

"A New Chromogenic Endotoxin-Specific Assay Using Recombined Limulus Coagulation Enzymes and its Clinical Applications", Obayashi et al, *Clinca Chemica Acta*, 149 (1985), pp. 55–65.

*Primary Examiner*—Christine M. Nucker
*Assistant Examiner*—M. P. Woodward
*Attorney, Agent, or Firm*—Armstrong, Westerman, Hattori, McLeland & Naughton

[57] ABSTRACT

Measuring of endotoxin using a reaction of a horseshoe crab hemocyte lysate with endotoxin in a solution can be carried out in the presence of a water-soluble polysaccharide containing $\beta$-1,3-glucosidic linkage and/or a water-soluble polysaccharide derivative containing $\beta$-1,3-glucosidic linkage.

11 Claims, 3 Drawing Sheets

PROCESS FOR MEASURING ENDOTOXIN

BACKGROUND OF THE INVENTION

This invention relates to a process for measuring endotoxin by using a reaction of a hemacyte lysate (amoebocyte lysate) of horseshoe crab (hereinafter abbreviated as "AL") with endotoxin, in which a factor present in AL which reacts with $\beta$-1,3-glucan to cause coagulation reaction (hereinafter referred to as "$\beta$-1,3-glucan sensitive factor") is inactivated, and the endotoxin alone is specifically measured.

Endotoxins are lipopolysaccharides present mainly in cell wall of Gram-negative bacteria and are known as pyrogens. Therefore, the measurement of endotoxin concentration in a sample is one important measurement in the fields of medical science, pharmacy and microbiology.

At present, as a method for measuring endotoxin, the so-called Limulus test utilizing the phenomenon that an extracted AL solution (hereinafter abbreviated as "AL solution") is activated by endotoxin to form gel clot is widely employed because of its simplicity, convenience, low cost, etc.

However, it was found that AL solution reacts not only with endotoxins but also with carboxymethylated $\beta$-1,3-glucan to undergo coagulation [Kakinuma et al., Biochem Biophys. Research Communication, 101 (2), 434–439 (1981)]. It was proved that this phenomenon is caused by the reaction of $\beta$-1,3-glucan sensitive factor present in AL solution with $\beta$-1,3-glucan or a derivative thereof (Iwanaga et al., Bacterial Endotoxin, published by Verlag Chemic, 365–382,1984).

Therefore, most of commercially available Limulus test reagents react not only with endotoxins but also with $\beta$-1,3-glucan, so that it is difficult to judge which of endotoxin, $\beta$-1,3-glucan and a mixture thereof is present in a sample, by the Limulus test. Thus, the specificity of such Limulus test reagents is a problem.

In order to solve this problem, there has been reported a method for preparing a reagent specific for endotoxins by removing $\beta$-1,3-glucan sensitive factor from AL solution [Japanese Patent Appln. Kokai (Laid-Open) Nos. 58-13516 and 59-27828]. However, all the methods disclosed in these references require a very troublesome procedure of treating AL solution, for example, by a gel filtration method or a chromatographic method using a carrier having heparin, dextran sulfate or the like attached thereto, to separate the AL solution into a fraction of proclotting enzyme, a fraction of $\beta$-1,3-glucan sensitive factor, and a fraction of a factor which reacts with endotoxin to cause coagulation (hereinafter abbreviated as "endotoxin sensitive factor"), and to remove the $\beta$-1,3-glucan sensitive factor. Therefore, for preventing AL solution or the fractions obtained therefrom from being contaminated by endotoxin during the separation procedures, there are required, for example, facilities used exclusively for carrying out said procedures. Moreover, the above methods are further disadvantageous in that the individual fractions should be properly mixed again in order to obtain a reagent specific for endotoxin.

On the other hand, the above reference of Kakinuma et al. [Biochem. Biophys. Research Communication, 101 (2), 434–439 (1981)]describes the following fact. AL solution reacts not only with endotoxin but also with carboxymethylated $\beta$-1,3-glucan to undergo coagulation reaction, but when carboxymethylated $\beta$-1,3-glucan is added in a large amount (10 $\mu$g/ml or more), it does not cause coagulation reaction, and when a large amount (10 ng/ml) of endotoxin is further added to the solution, coagulation reaction still occurred. However, the amount (10 ng/ml) of endotoxin added in said reference is as large as about 200 times the permissible concentration of endotoxin in distilled water for injection or the like [for example, the standard value (the permissible concentration in a sample) of endotoxin according to the XX edition of U.S. Pharmacopeia (USP) is or 0.05 ng/ml)]. Since such an amount is far greater than the amount which is normally measured as endotoxin using AL solution, application of the above fact for measuring endotoxin has been inconceivable.

SUMMARY OF THE INVENTION

This invention is intended to provide a process for measuring endotoxin alone specifically and quantitatively with ease and high efficiency without any influence of $\beta$-1,3-glucan sensitive factor present in AL.

This invention provides a process for measuring endotoxin by using a reaction of a horseshoe crab hemocyte lysate with endotoxin in a solution, characterized in that a water-soluble polysaccharide containing $\beta$-1,3-glucosidic linkage and/or a water-soluble poly-saccharide derivative containing $\beta$-1,3-glucosidic linkage is present in a reaction solution for reacting AL with endotoxin.

DESCRIPTION OF THE PREFERRED EMBODIMENTS

In the course of study on a method which permits easy and efficient preparation of a reagent specific for endotoxin by use of AL solution as starting material, the present inventors found the following fact. When a large amount of a water-soluble polysaccharide containing $\beta$-1,3-glucosidic linkage (hereinafter abbreviated as "GLPS") and/or a water-soluble polysaccharide derivative containing $\beta$-1,3-glucosidic linkage (hereinafter abbreviated as "GL-D") is present in a reaction solution for measuring endotoxin using AL solution, coagulation reaction of the AL solution by $\beta$-1,3-glucan is inactivated, but endotoxin still causes coagulation reaction. Because $\beta$-1,3-glucan sensitive factor is inactivated, so that no coagulation reaction of the AL solution by $\beta$-1,3-glucan occurs. However, as endotoxin sensitive factor and proclotting enzyme are not affected by the presence of GLPS and/or GL-D at all, surprisingly, endotoxin in a very slight amount of less than 0.01 EU/ml (0.002 ng/ml) can be detected specifically with high sensitivity. On the basis of the above finding, this invention has been accomplished.

As the GLPS and GL-D which are usable in this invention, any polysaccharides can be used without particular limitation so long as they contain β-1,3-glucosidic linkage and are soluble in water. Preferable examples of the GLPS include natural polysaccharides obtained from cell walls of, for example, various bacteria (e.g. Alcaligenes genus, Agrobacterium genus, etc.), yeasts (e.g. Saccharomyces genus, etc.), and mushrooms (e.9. a shiitake (*Cortinellus shiitake*), *Schizuphyrum commune, Coriolus versicolor*, etc.), specific examples of the natural polysaccharides including curdlan, pachyman, scleratan, leutinan, schizophyllan, coriolan, etc.; storage polysaccharides of algae, e.g. brown algae, Euglena, diatoms, etc., specific examples of the storage polysaccharides including laminaran, laminarin, paramilon, etc.; and preferable examples of GL-D include a polysaccaride derivative obtained by introducing at least one group selected from a carboxymethyl group, a carboxyethyl group, a methyl group, a hydroxyethyl group, a hydroxypropyl group, a sulfopropyl group, etc. into the natural polysaccharides or the storage polysaccharides according to a conventional method, for instance, any of the methods described, for example, in Munio Kotake "Daiyukikagaku" Vol. 19. 7th ed. Asakura Shoten, May 10, 1967, p. 70–101; A.E. Clarke et al., Phyto-chemistry, 1, 175–188 (1967); and T. Sasaki et al. Europ. J. Cancer, 15, 211–215 (1967). These natural polysaccharides, storage polysaccharides and derivatives thereof may be used singly or in combination of two or more of them.

As the AL solution usable in this invention, any one can be exemplified without particular limitation so long as it is extracted from hemocytes of horseshoe crab belonging to Limulus genus, Tachypheus genus or Carcinoscorpius genus and reacts with endotoxin to undergo coagulation reaction. It is, of course, possible to use AL solution prepared from freeze-dried products of AL solutions which are commercially available, for example, from Associates of Cape Cod Inc. (ACC).

As a method for allowing GLPS and/or GL-D to exist in a reaction solution of AL and endotoxin, there are exemplified, for example, a method comprising dissolving the GLPS and/or GL-D thereof in water, a buffer solution, a diluted alkali solution, or the like, and dissolving a freeze-dried product of AL in the resulting solution; a method comprising adding a solution of the GLPS and/or GL-D which is prepared by such a method as described above, to an AL solution prepared by dissolving a freeze-dried product of AL in distilled water for injection or a buffer solution; a method comprising adding the GLPS and/or GL-D to a sample; and a method comprising dissolving a reagent obtained by freeze-drying an AL solution containing a required amount of the GLPS and/or GL-D previously added, in distilled water for injection or a buffer solution. The method for allowing GLPS and/or GL-D to exist in a reaction solution of AL and endotoxin is not limited to these methods, and any method may be employed so long as the GLPS and/or GL-D is finally present in the reaction solution for reacting AL with endotoxin, in such an amount that the GLPS and/or GL-D inhibits β-1,3-glucan sensitive factor in AL solution but does not inhibit the reaction of endotoxin with endotoxin sensitive factor and the coagulation reaction of the AL solution which is caused by that reaction.

Although the concentration of GLPS and/or GL-D in the reaction solution is varied a little depending on, for example, production lot and detection sensitivity (EU/ml) for endotoxin of AL solution freeze-dried product or AL solution, it is usually 100 ng/ml to 100 mg/ml, preferably 10 μg/ml to 10 mg/ml in the reaction solution. AL solutions for measuring endotoxin which are prepared from the above-mentioned commercially available freeze-dried products of AL have a detection sensitivity for endotoxin of 0.03 to 5 EU/ml, and they undergo coagulation reaction when a polysaccharide containing β-1,3-glucosidic linkage and/or a derivative thereof is added in an amount of 0.1 to 1000 ng/ml. The concentration of GLPS and/or GL-D added to such AL solutions for the object of this invention is preferably 1000 times or more as high as a concentration of a polysaccharide containing β-1,3-glucosidic linkage and/or a derivative thereof at which the polysaccharide and/or derivative thereof causes coagulation reaction of the AL solutions.

In the method for measuring endotoxin of this invention, endotoxin may be measured according to a conventional endotoxin measuring method using AL solution, except for the presence of a predetermined amount of GLPS and/or GL-D in a reaction solution for reacting AL with endotoxin. Other reagents and the like used in the method of this invention ma be properly chosen in accordance with reagents used in a conventional endotoxin measuring method. More in detail, endotoxin can be measured as follows.

i Gel-clot technique

This technique comprises mixing AL solution with a sample in the presence of GLPS and/or GL-D, incubating the resulting mixture at a temperature of 0° to 40° C., preferably 25° to 40° C., for a predetermined time, and judging with the naked eye whether a gel is produced by coagulation or not.

ii End point-turbidimetric technique

This technique comprises mixing AL solution with a sample in the presence of GLPS and/or GL-D, incubating the resulting mixture at a temperature of 0° to 40° C., preferably 25° to 40° C., for a predetermined time, and measuring a turbidity due to coagulation using a coagulometer, a nepherometer, a spectrophotometer, or the like.

iii Kinetic tubidimetric technique

This technique comprises mixing AL solution with a sample in the presence of GLPS and/or GL-D, incubating the resulting mixture at a temperature of 0° to 40° C., preferably 25° to 40° C., for a predetermined time, and measuring a time required for a turbidity change due to coagulation to reach a designated value or a ratio in change of the turbidity using a coagulometer, a nepherometer, a spectrophotometer, or the like.

iv Chromogenic technique

This technique comprises mixing AL solution with a sample in the presence of GLPS and/or GL-D and a synthetic substrate such as Boc-Val-Leu-Gly-Arg-p-nitroaniline, Boc-Val-Leu-Gly-Arg-[(4-N-ethyl-N-2-hydroxyethyl) aminoaniline, etc of protease which is activated by the reaction of a component of the AL solution with endotoxin, incubating the resulting mixture at a temperature of 0° to 40° C., preferably 25° to 40° C., for a predetermined time, then if necessary adding a stopper for protease reaction, and measuring a substance released from the synthetic substrate by protease activity colorimetrically, or the like. The range of application of this invention is not limited to these methods, and this invention is applicable to any measuring method utilizing a reaction of AL with endotoxin.

In the measuring method of this invention, as the pH at the time of measurement, any pH may be employed so long as it does not inactivate the factors which reacts with endotoxin in AL solution to cause coagulation reaction, though a pH in the range of 6 to 8 is usually preferably employed. As the temperature at the time of measurement, any temperature may be employed so long as it does not inactivate the factors which reacts with endotoxin in AL solution to cause coagulation reaction, though a temperature of 0° to 40° C., preferably 25° to 40° C. is usually employed.

This invention is more concretely illustrated by way of the following examples, in which percents are all by weight unless otherwise specified.

REFERENCE EXAMPLE 1

Preparation of carboxymethylated curdlan

To 60 g of curdlan (available from Wako Pure Chemical Industries, Ltd.) were added 540 ml of toluene and 60 ml of ethanol, followed by adding thereto dropwise 61 g of a 50% aqueous sodium hydroxide solution, and the resulting mixture was heated at 50° C. and stirred for 1 hour. A solution of 35 g of monochloroacetic acid in 100 ml of a mixed solvent of toluene and ethanol in the ratio of 9:1 was added to the mixture, and the resulting mixture was stirred at 50° C. for another 1 hour. This reaction mixture was subjected to two repetitions of the above procedure of adding aqueous sodium hydroxide solution and monochloroacetic acid solution, thereafter cooled, and allowed to stand overnight. The reaction mixture was then poured into 1 liter of 90% methanol, and the precipitate formed was collected by filtration and dried to obtain 142 g of crude crystals. The crude crystals obtained were dissolved in 1420 ml of distilled water, and the pH of the resulting solution was adjusted to 8 with diluted hydrochloric acid. To this solution was added dropwise 12.78 liters of methanol with stirring, and the precipitate formed was collected by filtration, washed with 500 ml of 90% methanol, and then dried to obtain the desired compound carboxymethylated curdlan (hereinafter abbreviated as "CMCU").

EXAMPLE 1

Samples

The following curdlan solutions and endotoxin solutions were used as samples.

Curdlan solutions

There were used solutions prepared by dissolving curdlan containing non-detectable amount of endotoxin (available from Wako Pure Chemical Industries, Ltd.) in a 50 mM endotoxin free aqueous sodium hydroxide solution, to a concentration of 5 mg/ml, and diluting the resulting solution properly with distilled water for injection.

Endotoxin solutions

There were used solutions prepared by dissolving *Esoheriohia coli* control standard endotoxin (a lipopolysaccharide derived from *E. coli* UKT-B strain, available from Wako Pure Chemical Industries, Ltd.; each vial contained the lipopolysaccharide in an amount corresponding to 500 ng of FDA reference standard endotoxin EC-2; for dissolution in 5 ml) in 5 ml of distilled water for injection, and diluting the resulting solution properly with distilled water for injection.

Preparation of CMCU LAL solution

A freeze-dried product of AL solution derived from horseshoe crab belonging to Limulus genus (hereinafter the freeze-dried product being abbreviated as "LAL"; available from Wako Pure Chemical Industries, Ltd.; coagulation sensitivity 0.5 EU/ml; for dissolution in 5 ml) was dissolved in 5 ml of a solution prepared by dissolving the CMCU obtained in Reference Example 1 in distilled water for injection to a concentration of 0.2 mg/ml, whereby a CMCU-LAL solution was obtained.

Measuring procedure

To 0.1 ml of the CMCU-LAL solution was added 0.1 ml of each sample, and after sufficient mixing, a time (minutes) required for reducing the transmittance by 5% (hereinafter abbreviated as "Tg") was measured at 37° C. by means of a Toxinometer ET-201 (mfd. by Wako Pure chemical Industries, Ltd.).

Results

Figure 1:
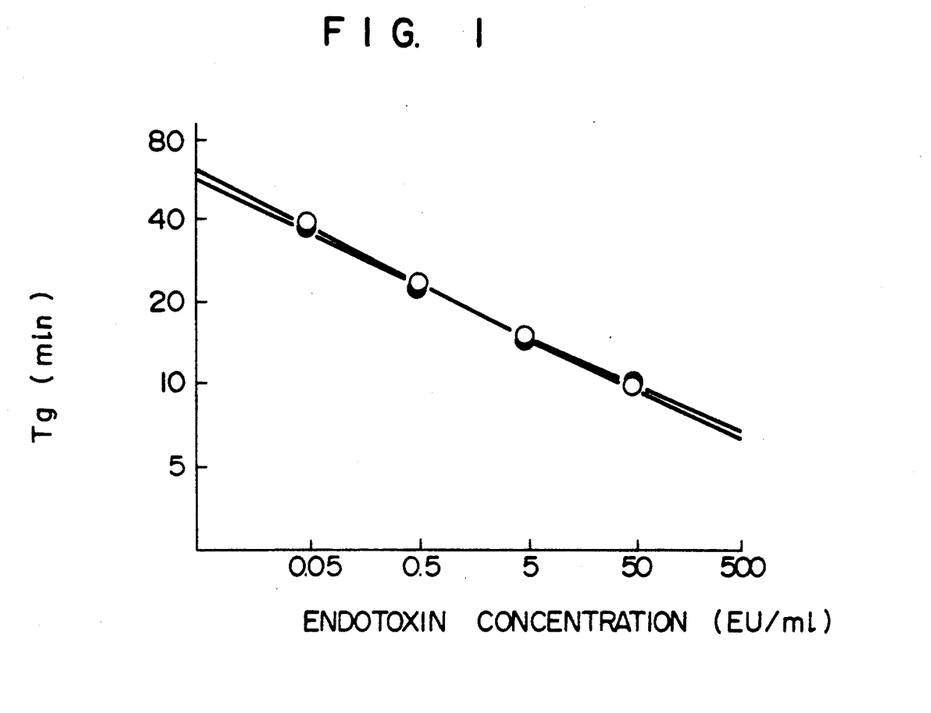
FIG. 1 shows calibration curves for endotoxin which were obtained in Example 1 and Comparative Example 1.

In FIG. 1, a calibration curve shown by —O— is obtained by plotting Tg value on the axis of ordinate corresponding to individual endotoxin concentrations (EU/ml) on the axis of abscissa. When the curdlan solutions were used as samples, the transmittance of the sample was not reduced by 5% in 80 minutes at any of the curdlan concentrations (data was not shown).

COMPARATIVE EXAMPLE 1

Measurement was carried out for the same samples as in Example 1 in exactly the same manner as in Example 1, except that a LAL solution prepared by dissolving LAL of the same lot as in Example 1 in 5 ml of distilled water for injection (hereinafter abbreviated as "untreated LAL solution") was used in place of the CMCU-LAL solution used in Example 1.

Results

Figure 2:
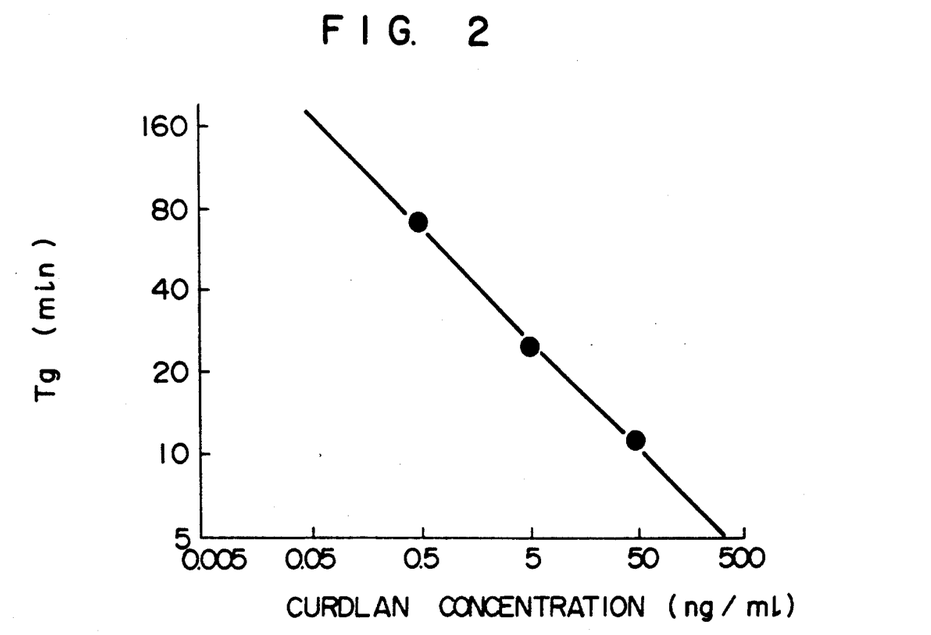
FIG. 2 shows a calibration curve for curdlan which was obtained in Comparative Example 1.

In FIG. 1, a calibration curve shown by —●— is obtained by plotting Tg value on the axis of ordinate corresponding to individual endotoxin concentrations on the axis of abscissa. In FIG. 2 is shown a calibration curve obtained by plotting Tg value on the axis of ordinate corresponding to individual curdlan concentrations (ng/ml) on the axis of abscissa.

As is clear from FIG. 1, when the endotoxin solutions were used as samples, a calibration curve having a good linearity could be obtained by using either the CMCU-LAL solution or untreated LAL solution as a reagent for measuring endotoxin.

However, as is clear from FIG. 2, untreated LAL solution reacts also with the curdlan solutions to result in a calibration curve having a good linearity.

It can be seen that as is clear from the above results, a reagent specific for endotoxin can be obtained by adding CMCU to AL solution.

EXAMPLE 2

In Table 1 are shown the results of measurement carried out by the same measuring procedure as in Example 1 by using the sample containing 1.5 EU/ml of endotoxin prepared in Example 1 (sample-1) and a mixture of equal amounts of the sample containing 20 ng/ml of curdlan and the sample containing 3.0 EU/ml of endotoxin which had been prepared in Example 1 (sample-2).

COMPARATIVE EXAMPLE 2

In Table 1 are also shown the results of measurement carried out for the same samples as in Example 2 in exactly the same manner as in Example 2, except that the same untreated LAL solution as used in Comparative Example 1 was used in place of the CMCU-LAL solution used in Example 2.

TABLE 1

| Sample | Example 2 | Comparative Example 2 |
|---|---|---|
| | Tg (min.) | |
| Sample-1 | 21.9 | 22.2 |
| Sample-2 | 21.2 | 13.5 |

It can be seen that as is clear from the results shown in Table 1, when the CMCU-LAL solution is used as a reagent for measuring endotoxin, a Tg value substantially equal to that obtained for the endotoxin solution is obtained for the sample containing both endotoxin and curdlan, thereby indicating that, the CMCU-LAL solution does not react with curdlan. It can also be seen that when measurement is carried out using the untreated LAL solution as a reagent for measuring endotoxin, Tg is greatly reduced by the addition of curdlan to endotoxin solution, indicating that the untreated LAL solution reacts both endotoxin and curdlan.

EXAMPLE 3

Samples

The following curdlan solutions and endotoxin solutions were used as samples.

Curdlan solutions

There were used solutions prepared by dissolving curdlan containing non-detectable amount of endotoxin (available from Wako Pure Chemical Industries, Ltd.) in a 50 mM aqueous sodium hydroxide solution (endotoxin free but containing 0.2 mg/ml of CMCU) to a concentration of 5 mg/ml, and diluting the resulting solution properly with distilled water for injection containing 0.2 mg/ml of CMCU.

Endotoxin solutions

There were used solutions prepared by dissolving *Escherichia coli* control standard endotoxin (a lipopolysaccharide derived from *E. coli* UKT-B strain, available from Wako Pure Chemical Industries, Ltd.; each vial contained the lipopolysaccharide in an amount corresponding to 500 ng of FDA reference standard endotoxin EC-2; for dissolution in 5 ml) in 5 ml of distilled water for injection containing 0.2 mg/ml of CMCU, and diluting the resulting solution properly with distilled water for injection containing 0.2 mg/ml of CMCU.

Measuring procedure

To 0.1 ml of the same untreated LAL solution as used in Comparative Example 1 was added 0.1 ml of each sample, and after sufficient mixing, Tg was measured at 37° C. by means of a Toxinometer ET-201.

Results

Figure 3:
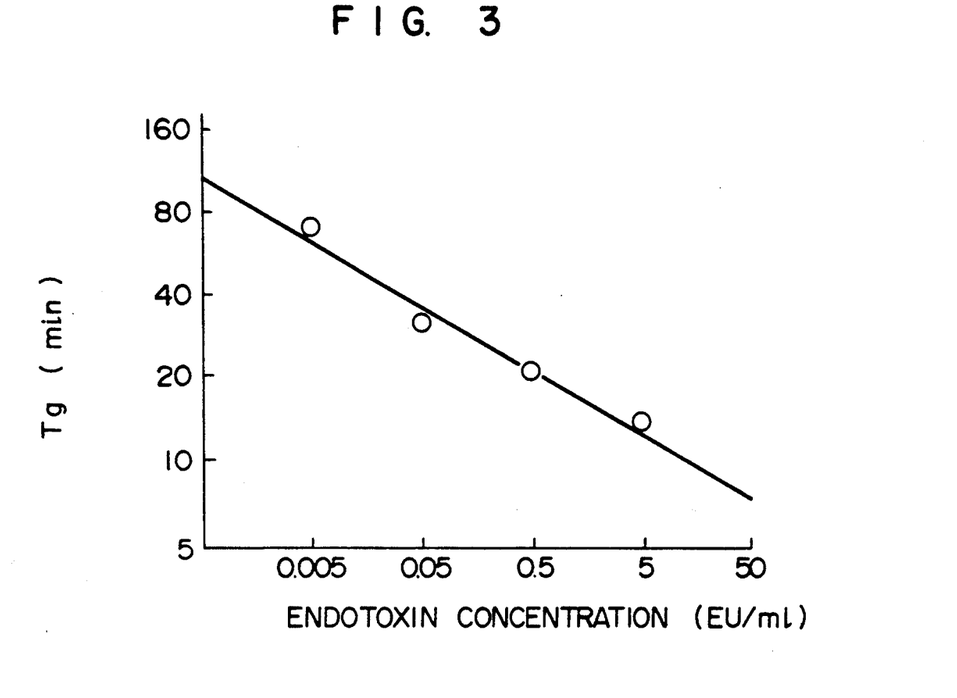
FIG. 3 shows a calibration curve for endotoxin which was obtained in Example 3.

In FIG. 3 is shown a calibration curve obtained by plotting Tg value on the axis of ordinate corresponding to individual endotoxin concentrations on the axis of abscissa. When the curdlan solutions were used as samples, the transmittance of the sample was not reduced by 5% in 80 minutes at any of the curdlan concentrations (data was not shown).

It can be seen that as is clear from these results, when CMCU is previously included in the samples, the untreated LAL solution does not react with curdlan but reacts only with endotoxin specifically.

EXAMPLE 4

In Table 2 are shown the results of measurement carried out by the same measuring procedure as in Example 3 by using the sample containing 1.5 EU/ml of endotoxin prepared in Example 3 (containing 0.2 mg/ml of CMCU) (samplβ-1) and a mixture of equal amounts of the sample containing 20 ng/ml of curdlan (containing 0.2 mg/ml of CMCU) and the sample containing 3.0 EU/ml of endotoxin (containing 0.2 mg/ml of CMCU) which had been prepared in Example 3 (sample-2).

COMPARATIVE EXAMPLE 3

By use of the same untreated LAL solution as used in Comparative Example 1, measurement was carried out by the same measuring procedure as in Example 4 by using, in place of the samples used in Example 4, the same samples as used in Example 2, i.e., the sample containing 1.5 EU/ml of endotoxin (containing no CMCU) (sample-3) and the mixture of equal amounts of the sample containing 230 ng/ml of curdlan (containing no CMCU) and the sample containing 3.0 EU/ml of endotoxin (containing no CMCU) (sample-4). The results obtained are also shown in Table 2.

TABLE 2

| Sample | Example 4 | Comparative Example 3 |
|---|---|---|
| | Tg (min.) | |
| Sample-1 | 21.6 | — |
| Sample-2 | 21.0 | — |
| Sample-3 | — | 22.2 |
| Sample-4 | — | 13.5 |

It can be seen that as is clear from the results shown in Table 2, when the sample containing CMCU is measured, a Tg value substantially equal to that obtained for the endotoxin solution is obtained even in the case where said sample contains curdlan in addition to endotoxin, namely, indicating that the inclusion of CMCU in the sample prevents the untreated LAL solution from reacting with curdlan. On the contrary when measurement is carried out using the sample containing no CMCU, Tg is greatly reduced by the addition of curdlan to endotoxin solution, indicating that the untreated LAL solution reacts also with curdlan.

EXAMPLE 5

Samples

The same as in Example 1.

CMCU-LAL solution

The same as in Example 1.

Measuring reagent

A measuring reagent was prepared by adding 1 ml of 0.45 M N,N-bis(2-hydroxyethyl)-2-aminoethane-sulfonic acid buffer (pH 7.5) and 1 ml of a substrate solution (containing 1.02 mM Boc-Val-Leu-Gly-Arg-[(4-N- ethyl-N-2-hydroxyethyl)aminoaniline (mfd. by Wako Pure Chemical Industries, Ltd.), 2.25 mM diethylaniline, and 0.12 M magnesium chloride]to 1 ml of the CMCU-LAL solution.

Measuring procedure

To 0.2 ml of the measuring reagent was added 0.1 ml of each sample, followed by sufficient mixing. The mixture was incubated at 37° C. for 30 minutes. After incubation, the reaction was stopped by adding 1 ml of a reaction stopper solution containing 0.17% sodium metaperiodate and 0.25% of sodium lauryl sulfate (SDS), and then absorbance at 730 nm of the reaction solution was measured.

Results

Figure 4:
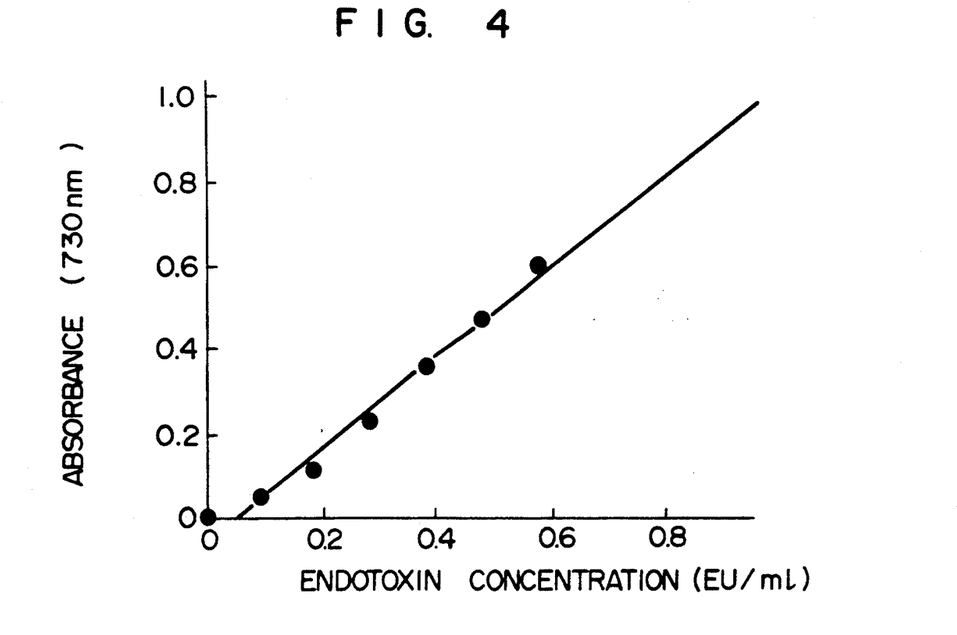
FIG. 4 shows a calibration curve for endotoxin which was obtained in Example 5.
Figure 5:
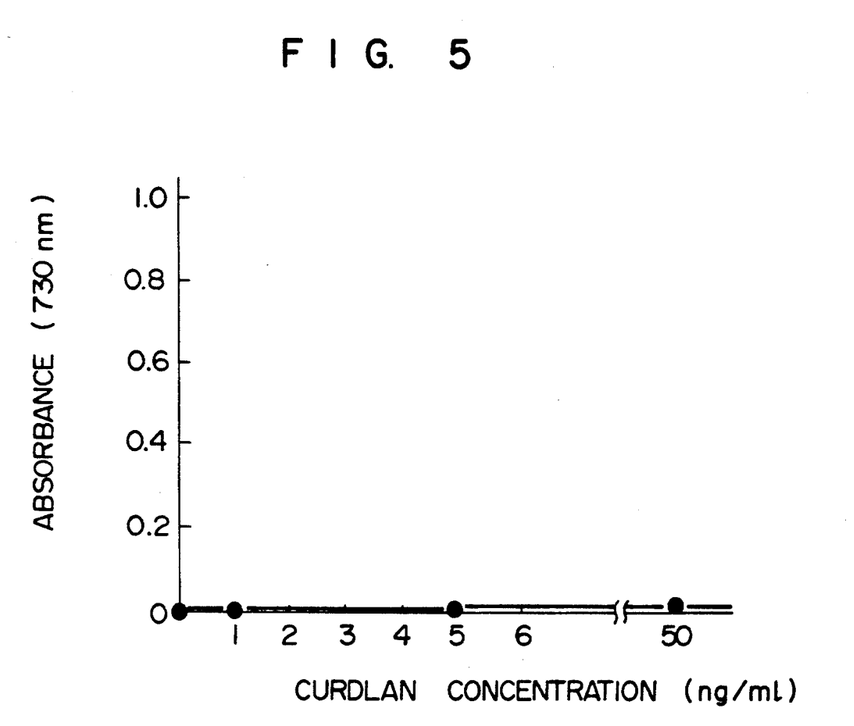
FIG. 5 shows a calibration curve for curdlan which was obtained in Example 5.

In FIG. 4 is shown a calibration curve obtained by plotting absorbance on the axis of ordinate corresponding to individual endotoxin concentrations on the axis of abscissa. In FIG. 5 is shown a calibration curve obtained by plotting absorbance on the axis of ordinate corresponding to individual curdlan concentrations on the axis of abscissa.

As is clear from FIG. 4 and FIG. 5, the CMCU-LAL solution according to this invention reacted with endotoxin and showed a calibration relation having a good linearity, but it did not react with curdlan at any concentration.

When measurement was carried out using a mixture of equal amounts of the sample containing 20 ng/ml of curdlan and the sample containing 1.0 EU/ml of endotoxin, absorbance at 730 nm of the reaction solution was 0.490, which was the same as that (0.486) measured for the sample containing 0.5 EU/ml of endotoxin alone.

It can be seen that as is clear from these results, the CMCU-LAL solution does not react with curdlan but is activated only by endotoxin.

As described above, this invention provides a process for measuring endotoxin using AL solution, which makes it possible to measure endotoxin alone specifically by inhibiting the β-1,3-glucan sensitive factor contained in AL solution easily and efficiently without any special procedure such as fractionation and recombination of components in the AL solution. Thus, this invention contributes greatly to the art.

What is claimed is:

1. In a process for measuring an amount of endotoxin in a sample containing an unknown amount of endotoxin by using a reaction of a horseshoe crab hemocyte lysate with endotoxin in a solution, the improvement which comprises carrying out the reaction in the presence of at least one water-soluble polysaccharide selected from the group consisting of curdlan, pachyman, scleratan, lentinan, schizophyllan, coriolan, laminaran, laminarin, paramilon and carboxyne thylated curdlan, in an mount sufficient to inactivate a factor present in the AL solution which reacts with beta-1,3-glucan, and determining the concentration of endotoxin in said unknown sample.

2. A process according to claim 1, wherein the water-soluble polysaccharide is present in the reaction solution in an amount of 100 ng/ml to 100 mg/ml.

3. A process for specifically measuring an amount of endotoxin in a sample containing an unknown amount of endotoxin which comprises mixing a solution of horseshoe crab hemocyte lysate with said sample in the presence of at least one water-soluble polysaccharide selected from the group consisting of curdlan, pachyman, scleratan, lentinan, schizophyllan, coriolan, laminaran, laminarin, paramilon and carbosymethylated curdlan, in an amount sufficient to inactive ate a factor present in the AL solution which reacts with beta-1,3-glucan, incubating the resulting mixture, judging a gel produced and determining the concentration of endotoxin in said sample.

4. A process for specifically measuring endotoxin, which comprises mixing a solution of horseshoe crab hemocyte lysate with a sample in the presence of at least one polysaccharide selected from the group consisting of curdlan, pachyman, scleratan, lentinan, schizophyllan, coriolan, laminaran, laminarin, paramilon and derivatives thereof, in an amount sufficient to inactivate a factor present in the AL solution which reacts with beta-1,3-glucan, incubating the resulting mixture, and measuring a turbidity due to coagulation.

5. A process for specifically measuring endotoxin, which comprises mixing a solution of horseshoe crab hemocyte lysate with a sample int eh presence of at least one water-soluble polysaccharide selected from the group consisting of curdlan, pachyman, scleratan, lentinan, schizophyllan, coriolan, laminaran, laminarin, paramilon and carboxcymethylated cardlan, in an amount sufficient to inactivate a factor present in the AL solution which reacts with beta-1,3-glucan, together with a synthetic substrate of protease, incubating the resulting mixture, and measuring a substance released from the synthetic substrate by protease activity.

6. A process for specifically measuring endotoxin, which comprises mixing a solution of horseshoe crab hemocyte lysate with a sample in the presence of at least one water-soluble polysaccharide selected from the group consisting of curdlan, pachyman, scleratan, lentinan, schizophyllan, coriolan, laminaran, laminarin, paramilon and derivatives thereof, in an amount sufficient to inactivate a factor present in the AL solution which reacts with beta-1,3-glucan, incubating the resulting mixture, ad measuring a time required for a turbidity change due to coagulation to reach a designed value or a ratio of change in the turbidity.

7. The process of claim 1, wherein said polysaccharide derivative is carboxymethyl curdlan.

8. The process of claim 3, wherein said polysaccharide derivatives is carboxymethyl curdlan.

9. The process of claim 4, wherein said polysaccharide derivative is carboxymethyl curdlan.

10. The process of claim 6, wherein said polysaccharide derivatives are obtained by introducing at least one of a carboxymethyl group, a carboxyethyl group, a methyl group, a hydroxyethyl group, a hydroxypropyl group and a sulfopropyl group into curdlan, pachyman, scleratan, lentinan, chizophyllan, coriolan, laminaran, laminarin or paramilon.

11. The process of claim 6, wherein said polysaccharide derivative is carbvoxymethyl curdlan.

* * * * *

UNITED STATES PATENT AND TRADEMARK OFFICE
CERTIFICATE OF CORRECTION

PATENT NO. : 5,179,006
DATED : January 12, 1993
INVENTOR(S) : Shuji Matuura, et al Page 1 of 3

It is certified that error appears in the above-indentified patent and that said Letters Patent is hereby corrected as shown below:

Column 2, line 10, after "(USP) is" insert --0.25 EU/ml--.

Column 3, line 7, change "e.9." to "e.g.";

line 10, "scleratan, leutinan" should read --sclerotan, lentinan--.

Column 4, line 22, change "ma" to --may--;

line 45, change "tubidimetric" to read --turbidimetric--;

line 60, change "etc" to --etc.--.

Column 5, line 63, change "Esoheriohia" to read --Escherichia--.

Column 8, line 16, "(sampl B-1)" should read --(sample-1)--.

Column 9, line 55, change "scleratan" to --sclerotan--;

line 56, change "carboxyne thylated" to read --carboxymethylated--;

line 57, change "mount" to --amount--.

UNITED STATES PATENT AND TRADEMARK OFFICE
CERTIFICATE OF CORRECTION

PATENT NO. : 5,179,006  
DATED : January 12, 1993  
INVENTOR(S) : Shuji Matuura, et al Page 2 of 3

It is certified that error appears in the above-indentified patent and that said Letters Patent is hereby corrected as shown below:

Column 10, line 7, change "scleratan" to read --sclerotan---;

line 8, change "carbosymethylated" to read --carboxymethylated--;

line 9, change "inactive ate" to read --inactivate--;

line 18, change "scleratan" to read --sclerotan--;

lines 19-20, change "derivatives thereof" to read --carboxymethylated curdlan--;

line 26, change "int eh" to read --in the--;

line 28, change "scleratan" to read --sclerotan--;

line 30, change "carboxcymethylated cardlan" to read --carboxymethylated curdlan--;

line 40, change "scleratan" to read --sclerotan--;

line 42, change "derivatives thereof" to read --carboxymethylated curdlan--;

line 45, change "ad" to read --and--;

UNITED STATES PATENT AND TRADEMARK OFFICE
CERTIFICATE OF CORRECTION

PATENT NO. : 5,179,006
DATED : January 12, 1993
INVENTOR(S) : Shuji Matsura, et al It is certified that error appears in the above-indentified patent and that said Letters Patent is hereby corrected as shown below:

Column 10, line 46, change "designed" to read --designated--;

lines 49, 51 and 53, change "carboxymethyl" to read --carboxymethylated--;

line 59, change "scleratan" to read --sclerotan--; change "chizophyllan" to read --schizophyllan--;

line 62, change "carbvoxymethyl" to read --carboxymethyl--

Signed and Sealed this

Twenty-ninth Day of November, 1994

Attest:

BRUCE LEHMAN

*Attesting Officer*   *Commissioner of Patents and Trademarks*